United States Patent [19]
Shanley et al.

[11] Patent Number: 5,626,230
[45] Date of Patent: May 6, 1997

[54] SHARPS KIT FOR PERCUTANEOUS CATHETERIZATION

[76] Inventors: Laurence M. Shanley; Hal Hansford; David Schultz, all of 20 NW. 181st St., Miami, Fla. 33169

[21] Appl. No.: 431,503

[22] Filed: Apr. 28, 1995

[51] Int. Cl.⁶ .................................................. B65D 81/00
[52] U.S. Cl. .......................................... 206/571; 206/366
[58] Field of Search .................................. 206/204, 570, 206/571, 365, 366; 604/192, 263, 283

[56] References Cited

U.S. PATENT DOCUMENTS

| | | |
|---|---|---|
| 3,008,570 | 11/1961 | Roehr et al. . |
| 4,742,910 | 5/1988 | Staebler . |
| 4,813,538 | 3/1989 | Blackman ........................ 206/366 X |
| 4,826,488 | 5/1989 | Nelson et al. . |
| 4,928,824 | 5/1990 | Barasch . |
| 4,936,449 | 6/1990 | Conard et al. ........................ 206/366 |
| 4,982,850 | 1/1991 | Mears . |
| 5,068,694 | 11/1991 | Wallace . |
| 5,069,666 | 12/1991 | Gericke . |
| 5,078,692 | 1/1992 | Cuprak . |
| 5,078,695 | 1/1992 | Farrar, Jr. . |
| 5,078,696 | 1/1992 | Nedbaluk . |
| 5,092,852 | 3/1992 | Poling . |
| 5,098,404 | 3/1992 | Collins . |
| 5,135,502 | 8/1992 | Koenig, Jr. . |
| 5,137,521 | 8/1992 | Wilkins . |
| 5,139,483 | 8/1992 | Ryan . |
| 5,141,500 | 8/1992 | Hake . |
| 5,201,418 | 4/1993 | Hanlon ........................ 206/366 |
| 5,207,667 | 5/1993 | Walker et al. . |
| 5,219,333 | 6/1993 | Sagstetter . |
| 5,292,314 | 3/1994 | D'Alessio . |
| 5,303,822 | 4/1994 | Wengyn et al. ........................ 206/571 X |
| 5,308,332 | 5/1994 | Dillard, III . |
| 5,311,985 | 5/1994 | Suida ........................ 206/366 X |
| 5,344,589 | 9/1994 | Miksic et al. ........................ 206/204 X |

*Primary Examiner*—Jacob K. Ackun
*Attorney, Agent, or Firm*—Herbert L. Lerner; Laurence A. Greenberg

[57] ABSTRACT

A sharps kit for percutaneous catheterization is formed as a flat housing with openings. The interior space is filled moisture adsorbing material such as sponge and silica gel. Hypodermic needles are inserted in openings of the housing and extending into the interior space. At least some of the needles can be flushed directly into the housing and they are wiped as they are inserted. The needles are provided with a luer lock with which they can be lockingly attached to a syringe. The housing has two protective conical shields pointed towards the openings.

5 Claims, 2 Drawing Sheets

SHARPS KIT FOR PERCUTANEOUS CATHETERIZATION

BACKGROUND OF THE INVENTION

Field of the Invention

The invention relates to a set of sharps and a container therefor used in catheterization by the Seldinger technique.

The Seldinger technique (named after a Swedish physician) is a method of percutaneous insertion of a catheter into an artery or a vein. Basically, the vessel in question is punctured with a needle, a thin wire is threaded through the needle and into the vessel. After the needle is withdrawn, a catheter is inserted over the wire. Finally, the wire is withdrawn and the catheter is in place.

A typical Seldinger insertion requires the handling of six different sharps. The protection of medical personnel while handling a needle attached to a conventional syringe during the process of removing the needle from the conventional protective sleeve or cap covering the needle or replacing the needle, after use, into the protective sleeve and for subsequent removal of the cap and needle from the barrel of the syringe for temporary storage or proper disposal has become increasingly important.

With the recognition of the existence of the HIV virus and the resulting development of the Acquired Immune Deficiency Syndrome (AIDS) the use, handling and disposal of hypodermic needles of the type attached to syringe type devices has become increasingly dangerous. Previously the medical profession was generally relaxed in the handling of such instruments as well as the overall disposal of the needle portion thereof after use. It is of course well recognized that various types of gloves, while generally protecting exposure of the covered skin to blood or other fluid from the body does not protect medical personnel from being inadvertently exposed to contaminated needles particularly when such needles are being replaced back into a conventional protective cap or sleeve after use and immediately prior to disposal.

Numerous attempts exist in the patented prior art to overcome such problems and provide adequate protection to medical personnel involved in such medical activities.

U.S. Pat. No. 5,078,692 to Cuprak, for instance, discloses a device for gripping, holding or stabilizing an article such as a needle secured to a hypodermic syringe and includes a hollow tubular stem which tapers to a graduated or step smaller tubular end or lumen toward the bottom. This bottom area has a flexible resilient spiral tail extending from the bottom end to facilitate various sized articles, objects or items being held by the non-dominant hand while performing certain work functions with the other hand and accordingly protecting the utilizing hand while performing such work functions.

U.S. Pat. No. 4,826,488 to Nelson, for instance, discloses a guard for hypodermic syringe needles which keeps the extremities and particularly the hands away from the syringe thereby attempting to prevent accidental punctures with contaminated needles. The needle guard includes a cylindrical cap which slides over the needle having a manipulating device to remove and replace the guard while keeping the hands away from the needle.

U.S. Pat. No. 5,098,404 to Collins discloses an apparatus for storing prior to and after use, a hypodermic syringe which includes a hypodermic needle such that the chance of the spread of infection of diseases is minimized. The device includes an elongated barrel with a stopper or penetrable cover through which the needle of the syringe structure is initially placed. After use the entry into the hollow chamber of the elongated tube is reversed and there is an antiseptic or like substance saturated within a plug or closure at the opposite end. A funnel like object or flared receiving portion is used to guide the needle into the interior of the tubular portion.

U.S. Pat. No. 5,078,695 to Farrar, Jr. discloses a needle cap holder of a syringe formed of a compressible material and having a central portion tapered inwardly from the top and bottom. The device is a central vertical cylindrical opening for receiving a needle cap of the syringe and it also includes a concaved bottom portion.

U.S. Pat. No. 5,092,852 to Poling discloses a safety syringe including a protective cap resiliently held on a needle of the syringe for preventing injuries, through punctures to someone handling the device. A locking tab is detachably clamped on a needle holder of the needle and at least a protrusion formed on the needle holder operably engages a protrusion groove formed in a needle sleeve. Removable of the locking tab from the needle holder and upon an inward depression of the needle holder and the needle into the needle sleeve engages the protrusion on the needle holder with the groove formed on the sleeve. The needle will therefore be permanently locked into the needle sleeve for a safer disposal of the needle after use.

Based on the above it is apparent that numerous attempts have been made in the medical profession in order to devise an efficient yet relatively inexpensive structure for the protection of the medical personnel's hands when utilizing needles, particularly needles associated with hypodermic syringes or like assemblies. Of particular danger is the period after use when the needle is "contaminated". Before disposal it is now required that the needle be replaced into a conventional protective cap or sleeve. The needle is "locked" in such sleeve and in certain instances may be removed from the barrel portion of the syringe for disposal. The past has indicated that if no protection device is utilized to accomplished the above set forth procedures, numerous punctures result which in turn results in contamination of medical personnel with the HIV virus or other contagious diseases. There is therefore a recognized need in the industry for a low cost device or assembly which adequately protects the personnel handling such hypodermic syringe structures wherein the device is efficient, reliable and is not complex from the standpoint of structural components or manufacture or assembly so that the cost of the overall device can be kept at an effective level. The device also may or may not be disposable or useable repeatedly.

Most cardiac catheterization is through the femoral artery with the Seldinger technique. Usually, a left side catheterization is followed by a right side catheterization. The flushing and temporary of the sharps between the two procedures is time consuming, complicated, and space and labor intensive. Also, the disposal of the plurality of sharps is cumbersome (No simple procedure kit has been previously proposed in the art).

SUMMARY OF THE INVENTION

It is accordingly an object of the invention to provide a sharps kit for percutaneous catheterization, which overcomes the hereinafore-mentioned disadvantages of the heretofore-known devices of this general type and which provides an integral kit specifically for a multi-sharps procedure with anti-stick protection and flushing capability. The main object is to provide an anti-stick assembly is specifically directed at the protection of medical personnel against punctures from a hypodermic needle associated with a conventional hypodermic syringe and ready accessibility of all sharps used in a certain technique.

With the foregoing and other objects in view there is provided, in accordance with the invention, a sharps kit for percutaneous catheterization, comprising:

a basic housing with walls defining an interior space therein; moisture adsorbing material disposed in the interior space;

the walls of the housing having openings formed therein;

a plurality of hypodermic needles inserted in the openings and extending into the interior space so as to allow flushing of the needles into the moisture adsorbing material; and each of the needles having Luer lock means for lockingly attaching to a syringe.

In accordance with an added feature of the invention, moisture adsorbing material is a sponge and/or silica gel.

In accordance with another feature of the invention, the plurality of hypodermic needles includes a two-part needle with a stylet and a cannula, and a plurality of anaesthetic needles of various lengths, typically used in the Seldinger technique. Additionally, the kit may be provided with a scalpel.

In accordance with a concomitant feature of the invention, the housing has a conical shield integrally formed thereon for facilitating an insertion of the needles into the openings, the conical shield having a conicity towards the openings. The shield acts as a protector and anti-stick measure.

A plurality of advantageous applications may be listed. Among them, multiple attempts for arterial or venous access is common and scalpel should be clean and the Selfinger needles should be cleaned and flushed in preparation for every attempt;

multiple sites for arterial and venous access is common and the scalpel and Seldinger needles should be flushed;

the sharps stay with one user; and the necessity to draw more Lidocaine with an 18$^G$ needle is not common.

Other features which are considered as characteristic for the invention are set forth in the appended claims.

Although the invention is illustrated and described herein as embodied in a sharps kit for percutaneous catheterization, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 2:
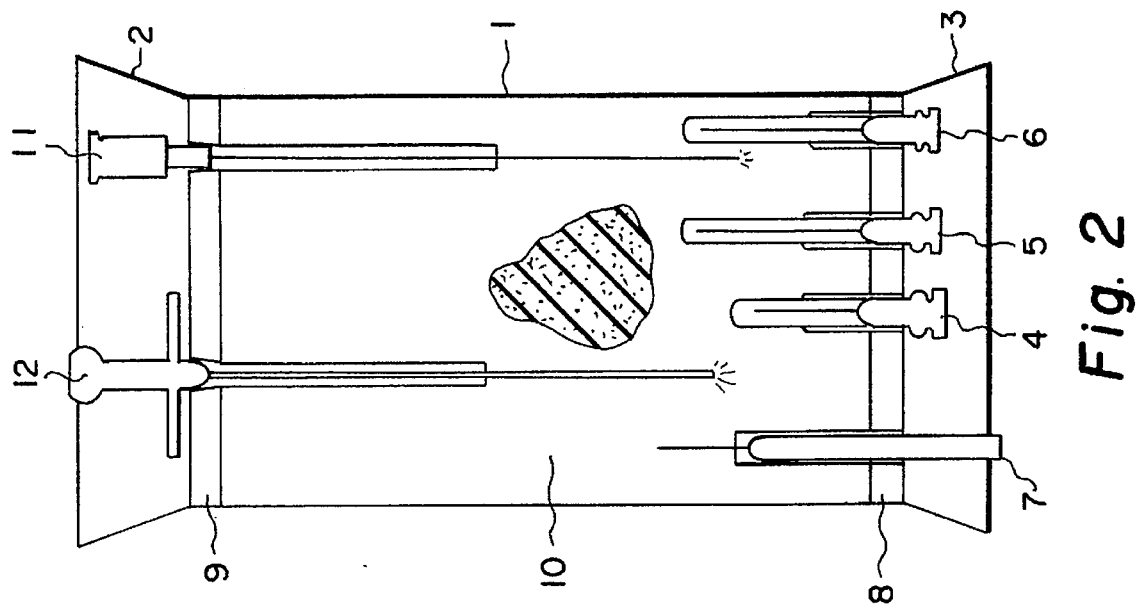
FIG. 2 is a cross-sectional view through the kit taken along a vertical plane in FIG. 1.
Figure 1:
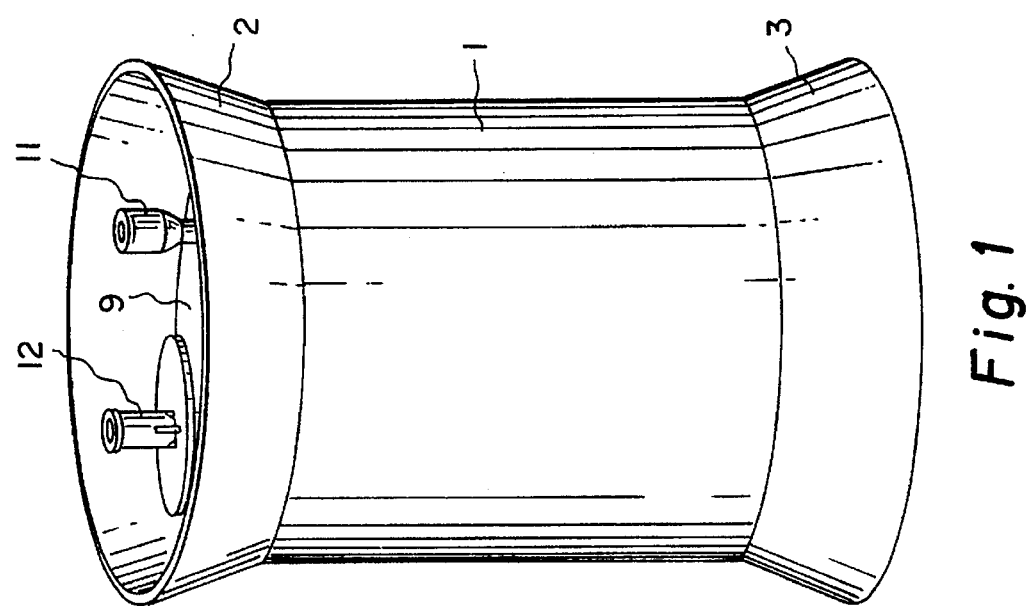
FIG. 1 is a perspective view of a kit according to the invention.

Referring now to the figures of the drawing in detail and first, particularly, to FIG. 1 thereof, there is seen a sharps kit according to the invention. The kit comprises a basic body 1 and two conical shields 2 and 3. The basic body 1 and the shields 2 and 3 are preferably formed as a single shell from a plastic of medium hardness. The form may be extruded, injection molded or manufactured by any similar process. Typical dimensions of the housing with the shields are 6½ by 3½ by 1½ inches.

A first needle 4 (18 gauge, 1½" needle) is used for drawing Lidocaine or the like from a vial. A second needle 5 (25 gauge, 1" needle) is used to localize superficial areas of the designated surgical site. A third needle 6 (21 gauge, 1½" needle) is used to localize deeper for the completion of the local anaesthesia. Each of the needles 4, 5 and 6 is disposed in its sheath and provided with a standard LUER lock for threaded connection with a syringe. The sheaths of the needles 4, 5 and 6 may be fully integrated in the housing or, alternatively, standard sheaths may be wedged into appropriate openings in the housing.

In preparing for catheterization, a scalpel 7 is used for cutting a pathway for access to the blood vessel in question. The housing 1 forms an interior space which is bordered by two housing lids 8 and 9. The lid 8 has openings formed therein for retaining the needles 4-6 and the scalpel 7. The interior space bounded by the lids 8 and 9 is filled with a adsorbent, i.e. moisture absorbing material, such as sponge material 10. Additionally, a supply of dehydrated silica gel may be disposed at strategic locations, so as to accommodate a large supply of flushing medium from any of the needles. After the incision with the scalpel 7, the same is inserted into the corresponding opening and its blade is accordingly wiped off on the sponge material. It is thus automatically cleaned.

Figure 3:
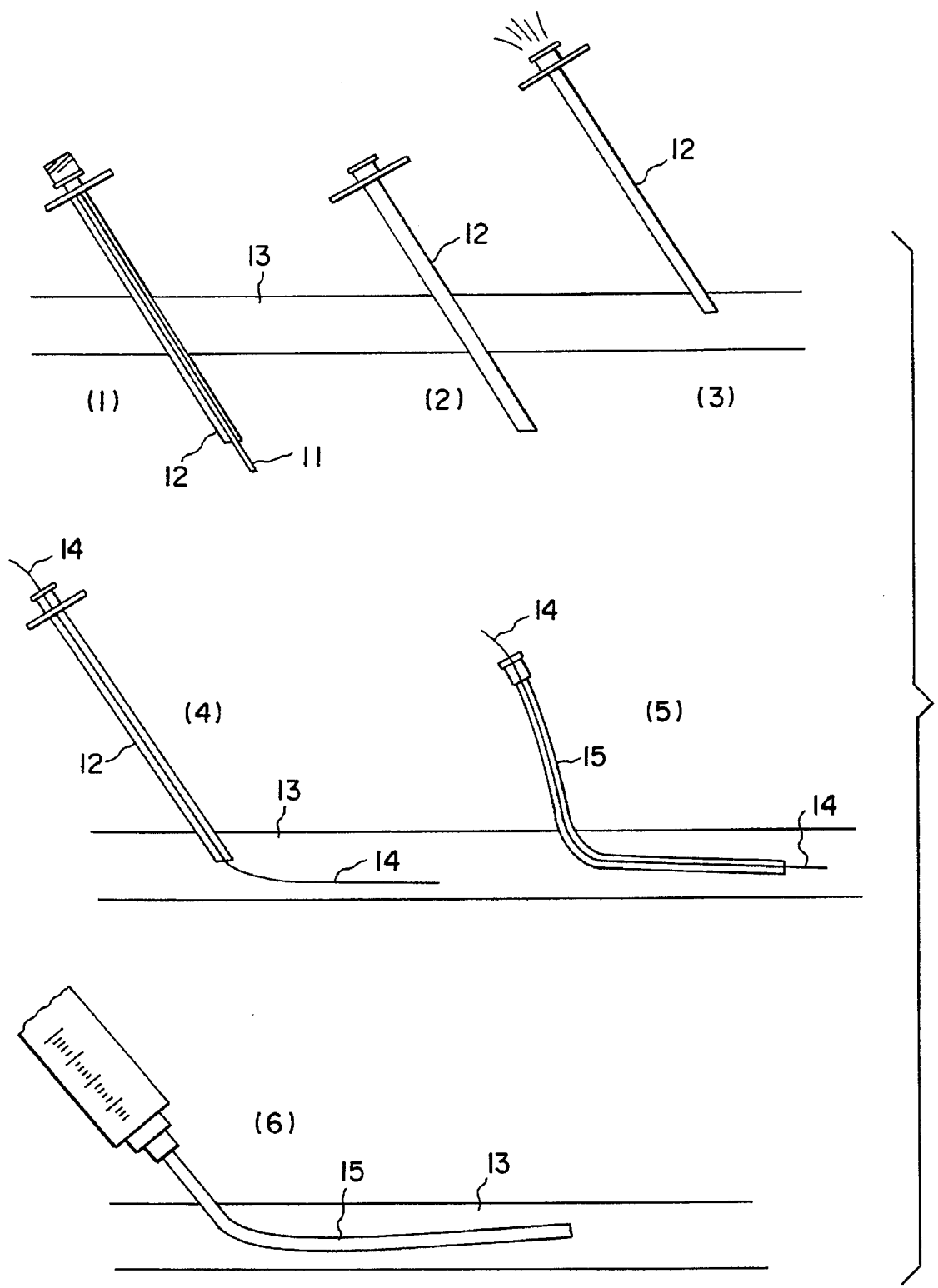
FIG. 3 is a sequential view of a Seldinger catheterization.

The lid 9 accommodates a two-part needle (Pott's needle), which comprises an inner stylet 11 which can be inserted into an outer cannula 12. With reference to FIG. 3, Seldinger catheterization uses the following sequence: (1) The two-part needle 11/12 is pushed through an artery 13. (2) The inner stylet 11 is pulled out. (3) The outer cannula 12 is pulled back until its opening is inside the artery 13. Its proper placement is detected when blood pumps through its opening. (4) A wire 14 is threaded through the needle 12 into the artery, and the needle 12 is pulled. (5) A catheter 15 is placed over the wire and inserted into the artery 13. (6) After the wire 14 has been pulled, the catheter 15 is in place and arterial access is complete.

As the stylet 11 and the cannula 12 of the two-part needle are removed, they must be flushed and wiped in preparation for another arterial or venous access. This can be done with this invention, by inserting and flushing directly into the moisture absorbant, such as the sponge 10 and/or the silica gel, in the housing 1. After removal from the surgical site, a flushing medium is drawn through the needle into a syringe, the needle is inserted into its location in the housing (while it is still locked to the syringe) and the syringe plunger is pushed, so that the needle is flushed into the sponge 10. The stylet 11 and the cannula 12 are provided with a luer lock for that purpose. They cannot be properly flushed otherwise.

With the kit according to the invention, all of the sharps necessary for catheterization can be safely handled and temporarily stored in easy reach of the surgical procedure. At the same time, it is not necessary to remove any of the sharps for wiping and flushing. Finally, the kit can be disposed of as a whole into the sharps container for proper disposal.

We claim:

1. A sharps kit for percutaneous catheterization, comprising:

a basic housing with walls defining an interior space therein; moisture adsorbing material disposed in said interior space;

said walls of said housing having openings formed therein; a plurality of hypodermic needles inserted in said openings and extending into said interior space so as to allow flushing of said needles into said moisture adsorbing material, said plurality of hypodermic needles including a two-part needle with a stylet and a cannula, and a plurality of anaesthetic needles of various lengths; and each of said needles having Luer lock means for lockingly attaching to a syringe.

2. The sharps kit according to claim 1, wherein said moisture adsorbing material is a sponge.

3. The sharps kit according to claim 1, wherein said moisture adsorbing material is silica gel.

4. The sharps kit according to claim 1, which further comprises a scalpel disposed in one of said openings.

5. The sharps kit according to claim 1, which further comprises a conical shield integrally formed on said housing for facilitating an insertion of said needles into said openings, said conical shield having a conicity towards said openings.

* * * * *